(12) United States Patent
Mao et al.

(10) Patent No.: US 7,999,106 B2
(45) Date of Patent: Aug. 16, 2011

(54) PROCESSES FOR THE PREPARATION OF CLOPIDOGREL HYDROGEN SULFATE POLYMORPHIC FORM I

(75) Inventors: Haifang Mao, Shanghai (CN); Hongguang Qian, Shanghai (CN); Chen Chen, Shanghai (CN)

(73) Assignee: KRKA, Tovarna Zdravil, D.D., Novo Mesto, Novo Mesto (SI)

( * ) Notice: Subject to any disclaimer, the term of this patent is extended or adjusted under 35 U.S.C. 154(b) by 1079 days.

(21) Appl. No.: 11/568,075

(22) PCT Filed: Apr. 19, 2005

(86) PCT No.: PCT/EP2005/004160
§ 371 (c)(1),
(2), (4) Date: Feb. 15, 2007

(87) PCT Pub. No.: WO2005/100364
PCT Pub. Date: Oct. 27, 2005

(65) Prior Publication Data
US 2009/0234123 A1    Sep. 17, 2009

(30) Foreign Application Priority Data

Apr. 19, 2004  (CN) .......................... 2004 1 0009028
Apr. 21, 2004  (SI) ....................................... 20040122

(51) Int. Cl.
*C07D 471/02*     (2006.01)

(52) U.S. Cl. ....................................................... 546/114
(58) Field of Classification Search ................... 546/114
See application file for complete search history.

(56) References Cited

U.S. PATENT DOCUMENTS

| 4,847,265 A | 7/1989 | Badorc et al. |
| 6,429,210 B1 | 8/2002 | Bousquet et al. |
| 2006/0069130 A1 | 3/2006 | Kubota et al. |

FOREIGN PATENT DOCUMENTS

| EP | 0281459 | 9/1988 |
| EP | 1087976 | 4/2001 |
| WO | WO 99/65915 | 12/1999 |
| WO | WO 03/051362 | 6/2003 |
| WO | WO 2004/020433 | 3/2004 |
| WO | WO 2004/048385 | 6/2004 |
| WO | WO 2004/081016 | 9/2004 |
| WO | WO 2005/003139 | 1/2005 |
| WO | 2005/104663 | * 11/2005 |

OTHER PUBLICATIONS

Bernstein "Polymorphism in molecuiar crystals" Oxford:Clarendon Press 117-118,272& 273 (2002).*

* cited by examiner

*Primary Examiner* — Patricia Morris
(74) *Attorney, Agent, or Firm* — Swanson & Bratschun, L.L.C.

(57) ABSTRACT

Processes for the preparation of clopidogrel hydrogen sulfate of polymorphic form I are described which include use of specific solvents and process measures to avoid formation of undesired by-products.

23 Claims, No Drawings

PROCESSES FOR THE PREPARATION OF CLOPIDOGREL HYDROGEN SULFATE POLYMORPHIC FORM I

RELATED APPLICATIONS

This application is a 35 U.S.C. §371 national phase application of PCT/EP2005/004160 (WO 2005/100364), filed on Apr. 19, 2005, entitled "Processes For The Preparation of Clopidogrel Hydrogen Sulfate Polymorphic Form I" which claims priority to Chinese Application Serial No 2004 1 0009028.8, filed Apr. 19, 2004 and Slovenia Application Serial No. P-20040122, filed Apr. 21, 2004. Each of these applications is specifically incorporated herein by reference in its entirety.

TECHNICAL FIELD

The present invention relates to processes for the preparation of clopidogrel hydrogen sulfate of polymorphic. Form I, i.e. methyl-(+)-S-α-(2-chlorophenyl)-4,5,6,7-tetrahydrothieno-[3,2-c]pyridine-5-acetate hydrogen sulfate of polymorphic form I, in particular from various clopidogrel salts.

The present novel processes make it possible to prepare a highly pure and stable form I material, in particular having a purity of at least 99%.

PRIOR ART

Clopidogrel hydrogen sulfate is a known valuable pharmaceutical substance used as a platelet aggregation inhibitor and was originally disclosed in EP 281 459. There is claimed a process for the preparation of clopidogrel hydrogen sulfate called polymorphic form I. In U.S. Pat. No. 6,429,210 there is disclosed the difference between the polymorphic forms I and II. In WO 03/051362 the new crystalline powder polymorphic forms III, IV, V, VI and the amorphous form of clopidogrel hydrogen sulfate as well as a process for the preparation of the forms I and II are disclosed. In the above literature the differences between various polymorphic forms of clopidogrel hydrogen sulfate were disclosed.

Different polymorphic forms have different characteristics, which depend upon the conformation and orientation of the molecules in the unit cell. The characteristics of the polymorphic forms can be determined by the following measuring methods:

FT-IR spectra, X-ray powder diffractograms, and DSC.

There are numerous further Prior Art publications, which are very broad, yet a very pure product may only be obtained at precisely defined conditions, which have been established by the inventors when contemplating the present invention.

TECHNICAL SOLUTION

The object of the invention is the development of new processes for obtaining a stable and pure clopidogrel hydrogen sulfate form I. In the following the first, the second and the third process found by the inventors will be explained.
The First Process The process for the preparation of clopidogrel hydrogen sulfate polymorphic form I having a purity of in particular at least 99% is characterized in that a clopidogrel salt, such as clopidogrel hydrochloride or a crystalline mixture of clopidogrel hydrogen sulfate or clopidogrel camphor sulfate, is neutralized, in particular with potassium carbonate, in an organic solvent, extracted, separated, the organic phase is dried and concentrated to the free clopidogrel base, the said base is brought into a dry solution with an organic solvent, cooled to a temperature of between −20° C. and +25° C. and then treated with 0.6 to 1.1 equivalents of concentrated sulfuric acid under controlling the temperature between −30° C. and +5° C. in order to achieve the crystallization of the precipitated clopidogrel hydrogen sulfate of form I.

The neutralisation can also be effected with other bases such as sodium hydrogen carbonate.

As the organic solvent for neutralisation with potassium carbonate, dichloromethane, chloroform, ethyl ether, t-butyl methyl ether, or isopropyl ether may be used.

As the organic solvent for dissolving the concentrated free clopidogrel base, methyl acetate, ethyl acetate, dichloromethane or t-butyl methyl ether may be used.

Preferably, the same solvent is used both in the neutralisation and in the dissolving of the concentrated free base.

Dichloromemane is the preferred solvent.

The precipitation may optionally be supported by seeding with form I crystals.

In the following, this first process will be disclosed in more detail by stating preferred embodiments.

Different clopidogrel salts, such as clopidogrel hydrochloride or a crystalline mixture of clopidogrel hydrogen sulfate or clopidogrel camphor sulfate, are introduced under inert gas atmosphere into a non-polar organic solvent to obtain a reaction mixture. It is cooled with ice water, then an aqueous potassium carbonate solution is added drop by drop into the reaction mixture, whereby an organic phase containing the clopidogrel-free base and an aqueous (upper) phase are obtained. The aqueous phase is controlled to have a pH value of more than 9, The upper aqueous phase is extracted preferably with the same solvent as above. The organic phases are combined and dried, e.g. over $Na_2SO_4$ or $MgSO_4$, and then concentrated to obtain the free clopidogrel base.

The concentrated clopidogrel base is dissolved in an organic solvent, such as methyl acetate, ethyl acetate, dichloromethane or t-butyl methyl ether, and stirred for some hours up to a complete dissolution. During this procedure the temperature should be well controlled between −20 and +25° C. Then a suitable quantity of concentrated sulfuric acid is introduced drop by drop into the complete solution and the temperature is controlled between −30 and +5° C.

After the completion of the dropwise addition, the reaction mixture is stirred for another 5-15 hours at a temperature between −5 and +15° C. It is filtered and washed preferably with the same solvent as above. It is dried in vacuo at temperatures between 30° C. and 70° C., preferably between 50° C. and 55° C., in order to obtain pure clopidogrel hydrogen sulfate form I as originally disclosed in EP 281 459.

It has an infrared spectrum with absorption bands at 2987, 1753, 1222, 1175 and 841 $cm^{-1}$, and a powder X-ray diffraction pattern with peaks at 9.2, 10.9, 15.2, 17.9, 18.5, 20.6, 23.0, 23.2, 23.4 and 25.5±0.2 degrees 2 Theta.

The advantages of the present process are:
  By the inventive process a highly pure and stable clopidogrel form I having a steady quality is obtained, whereas it is difficult to achieve the said advantage by Prior Art.
  The morphologically uniform product of the invention is stable after storage for 12 months.
  No special storing conditions are necessary. It may be stored under general conditions for pharmaceuticals.
  The inventive process can be readily scaled up and is suitable for industrial scale production.

The Second Process

This process for preparing pure and stable polymorphic form I of clopidogrel hydrogen sulfate includes the following steps:

(a) under the protection of inert gas (N2, Ar2) and cooling conditions, 0.01 to 0.05 mol (preferably 0.02 to 0.03 mol) clopidogrel salt is introduced in 50 to 300 ml (preferably 100 ml) organic Solvent A to obtain a reaction mixture, an aqueous potassium carbonate or sodium carbonate solution is added drop by drop into the reaction mixture with agitation, with the ratio of potassium carbonate or sodium carbonate to clopidogrel salt being 1.0 to 3.0 (preferably 1.2-1.5), to obtain an upper aqueous phase the pH value of which is controlled to more than 9.

(b) Whereby, an organic phase containing clopidogrel free base (lower) and aqueous (upper) phase are obtained after the process of step (a), the upper aqueous phase is extracted preferably with 30 to 150 ml Solvent A, the organic phases are combined and dried e.g. over sodium sulfate or potassium sulfate and then concentrated to obtain the free clopidogrel base.

(c) The concentrated clopidogrel base is dissolved in the organic Solvent B, and stirred for about one hour to a complete dissolution. During the procedure, the temperature is well controlled between −20 and 5° C. (preferably at −15 to −5° C.) The suitable quantity Sulfuric Acid Solution is introduced drop by drop into the complete solution and the temperature is controlled between −20 and 5° C. (preferably between −15 and −5° C.). After the completion of the drop wise addition, the reaction mixture is stirred for another 10 hours between a temperature of −20 and 20° C. (preferably −10 to 10° C.).

(d) The obtained reaction mixture is filtered and washed with solvent B for 4 times with a quantity of 10 ml each. It is dried in vacuo at a temperature of 40 to 70° C. (preferably 50 to 55° C.) and obtained is the pure clopidogrel hydrogen sulfate polymorphic of form I.

In step (a), the Clopidogrel Salt is either Clopidogrel Camphor Sulfate, or Clopidogrel HCl, or Clopidogrel Hydrogen Sulfate.

In step (a), Solvent A mentioned, can be Methylene Dichloride, Ethylene Dichloride, Chloroform, Ethyl Ether, tert-butyl methyl ether, isopropyl ether or optionally their mixture.

In step (c), Solvent B mentioned, can be Ethyl Ether, Methyl Acetate, Ethyl Acetate, Ethyl Formate, Isopropyl Ether, Methylene Dichloride, tert-butyl methyl ether.

In step (d), the Sulfuric Acid solution mentioned is either the different concentration degree solution of sulfuric acid in Solvent B or the 80% above concentrated sulfuric acid.

According to this process one can obtain the pure clopidogrel hydrogen sulfate industrially. The yield is around 50 to 85%, the melting point 181 to 186° C., and the specific rotation is between 52.0 and 55.0° (c=l, Methanol).

The clopidogrel hydrogen sulfate polymorphic form I obtained is characterized by the measurement of X-Ray powder diffraction, FT-Infrared Spectrum, and DSC.

It has an infrared spectrum with absorption bands at 2987, 1753, 1222, 1175 and 841 $cm^{-1}$; an X-ray powder diffraction pattern with peaks at 9.2, 10.9, 15.2, 17.9, 18.5, 20.6, 23.0, 23.4 and 25.5+0.2 degree 2 Theta.

An Analysis of differential Enthalpy (DSC) is performed out the right Chromatograph of melting point of form I.

The Third Process

This process for the preparation of clopidogrel hydrogen sulfate of polymorphic form I is characterized in that (a) optionally a clopidogrel salt is converted into clopidogrel base, (b) a solution of clopidogrel base in a solvent is provided, wherein the solvent is ethyl acetate, or a mixture of ethyl acetate with methylene chloride or with an ether, (c) the solution of clopidogrel base is reacted with sulfuric acid, and (d) clopidogrel hydrogen sulfate of form I is recovered.

In the optional step (a) a clopidogrel salt, like a salt with hydrochloric or sulfuric acid of any polymorphic form, such as form I, form II or amorphous form can be used. The conversion is normally accomplished by using a base and preferably the neutralising is performed with an aqueous inorganic base, such as sodium hydrogen carbonate, potassium carbonate or sodium carbonate.

It is preferred that the clopidogrel salt is dissolved in a solvent. This is preferably immiscible with water and is able to dissolve clopidogrel base. The solvent is in particular methylene chloride, chloroform or an alkyl acetate, such as ethyl acetate.

During the neutralisation a two phase system comprising an organic and an aqueous phase is normally formed. It is preferred that the pH of the aqueous phase is kept in the range of 7 to 8 in order to diminish formation of undesirable by-products. After separation of the phases and extraction of the water phase it is preferred that the combined organic phases are dried, for example over magnesium sulfate. It has been shown that such a drying is advantageous as the presence of water may promote formation of the undesirable form II material.

Even though the above-described step (a) is optional, it is preferred that this step is carried out in the process.

In step (b) a solution of clopidogrel base in a solvent is provided, wherein the solvent is ethyl acetate, or a mixture of ethyl acetate with methylene chloride or with an ether.

It is preferred that a mixture ethyl acetate with methylene chloride is used in this step which comprises up to 10% and preferably 1 to 5% by weight of methylene chloride.

Alternatively, it is also preferred that a mixture of ethyl acetate with an ether is used in this step which comprises up to 30% by weight of ether. The ether is preferably one which contains up to 10 carbon atoms.

In step (c) the solution of clopidogrel base is reacted with sulfuric acid.

For this purpose it is preferred that the sulfuric acid is used in form of a solution in an organic solvent, which preferably is ethyl acetate.

It is also preferred that the solution of sulfuric acid in the organic solvent is prepared at a temperature of less than 0° C. and preferably between −5 to −15° C. This measure helps to prevent formation of undesirable by-products, for example the production of monoethyl sulfate in case of use of ethyl acetate as organic solvent.

It is also preferred that the reaction mixture obtained after completion of the reaction has as organic solvents ethyl acetate with a content of up to 10, preferably 1 to 5 and most preferred 0.5 to 4.0% by weight of methylene chloride.

Further, it has shown to be advantageous if only up to 0.9 equivalents of sulfuric acid relative to clopidogrel base are used for the reaction. Higher amounts may lead to production of the undesirable form II.

Further, it is preferred that the temperature of the mixture obtained during the reaction with sulfuric acid is kept in the range of −20 to 5° C. and preferably −15 to 0° C. This as well as continuous stirring during the reaction are steps which have shown to be advantageous for the preparation of pure form I material.

It is further preferred that the reaction mixture obtained after completion of the reaction with the sulfuric acid is maintained for at least 1 hour, preferably 2 to 4 hours, at a temperature of −15 to 0° C., preferably −5 to 0° C., with stirring.

Further, it has shown to be beneficial that the reaction mixture obtained after completion of the reaction with sulfuric acid is slowly allowed to warm temperature with stirring and this is preferably effected by using a heating rate of 0.5 to 6° C., preferably 2 to 4° C. per hour.

In a typical such slow warming procedure the mixture is allowed to warm by 3° C. per hour to 13 to 17° C. in about 8 hours and then in about 8 hours it is slowly heated to 16 to 20° C.

It is also preferred that after completion of the reaction, the mixture is stirred for at least 15 hours. This has shown to be very advantageous for forming the desired crystals.

In step (d) the clopidogrel hydrogen sulfate of form I is recovered. This is in particular effected by filtering the precipitated material, washing it and drying the product, preferably in a vacuum at a temperature of 50 to 70° C. and preferably at 55 to 60° C.

The final product has shown to contain not more than 0.5% by weight of the undesired form II material.

The invention is illustrated, but not limited by the following Examples

Example 1

Under nitrogen gas, clopidogrel hydrochloride (7.15 g) was introduced into dichloromethane (100 ml) in a 250 ml reactor under stirring and cooling with ice water to obtain a mixture. Then a solution of potassium carbonate (2.5 g) in de-ionized water (30 ml) was added drop by drop into the reactor and it was stirred for one hour. The pH value of the upper aqueous phase was kept over 9. The organic phase was separated and the aqueous phase was extracted with dichloromethane (2×50 ml). The organic phases were combined, dried over $Na_2SO_4$ and concentrated to a free clopidogrel base, To the concentrated free base methyl acetate (150 ml) was added drop by drop and it was stirred for more than one hour until the free base of clopidogrel was completely dissolved.

The solution was cooled to a temperature between −15° C. and −5° C., then 90% sulfuric acid (2 g) was added drop by drop under controlling the temperature between −5° C. and 5° C. during the dropwise addition. After the completion of the dropwise addition the reaction mixture was stirred for another 10 hours. It was filtered and washed with methyl acetate (4×10 ml). It was dried in vacuo between 50° C. and 55° C. and clopidogrel hydrogen sulfate form I (5.6 g) with a specific rotation +54.1° (c=1, methanol), m.p. 182.3-183.5° C., was obtained in a yield of 64%.

Example 2

Under nitrogen gas, clopidogrel camphor sulfate (1 kg) was introduced into dichloromethane (10 l) in a 25 l glass reactor under stirring and cooling with cool salt water. Then a solution of potassium carbonate (0.31 kg) in de-ionized water (5 l) was added drop by drop into the reactor and it was stirred for one hour. The pH value of the upper aqueous phase was kept over 9. The lower organic phase was separated and the aqueous phase was extracted with dichloromethane (2×5 l). The organic phases were combined and dried over $Na_2SO_4$ (1 kg) and then concentrated to obtain the free clopidogrel base. To the concentrated free base methyl acetate (15 l) was added drop by drop under stirring for one hour until the free clopidogrel base was completely dissolved.

The complete solution was cooled to a temperature between −15° C. and −5° C., then 95% sulfuric acid (2.1 kg) was added drop by drop at a temperature between −10° C. and 0° C. After the completion of the dropwise addition the reaction mixture was stirred for another 5 hours. It was filtered and washed with methyl acetate (3×1 l). It was dried in vacuo between 50° C. and 55° C. and clopidogrel hydrogen sulfate form I (5.6 kg) with a specific rotation +53.2° (c=1, methanol), m.p. 182.1-183.0° C., was obtained.

Example 3

Under nitrogen gas, a crystalline mixture of clopidogrel hydrogen sulfate (8.7 g) was introduced into dichloromethane (100 ml) in a 250 ml reactor under stirring and cooling with cool water. Then a solution of potassium carbonate (3 g) in de-ionized water (50 ml) was added drop by drop into the reactor and it was stirred for one hour. The pH value of the upper aqueous phase was kept over 9. The lower organic phase was separated and the aqueous phase was extracted with dichloromethane (2×50 ml). The organic phases were combined and dried over $Na_2SO_4$, then concentrated. To the concentrated free base, ethyl acetate (150 ml) was added and it was stirred for more than one hour until the free clopidogrel base was completely dissolved.

The complete solution was cooled to a temperature between −15° C. and −5° C., then 90% sulfuric acid (2 g) was added drop by drop at a temperature between −10° C. and 0° C. After the completion of the dropwise addition the reaction mixture was stirred for another 5 hours. It was filtered and washed with ethyl acetate (4×10 ml). It was dried in vacuo between 50° C. and 55° C. and clopidogrel hydrogen sulfate form I (4.3 g) with a specific rotation +53.5° (c=1, methanol), m.p. 182-183° C., was obtained in a yield of 57%.

Example 4

Under the protection of Argon Gas, clopidogrel hydrogen sulfate (12.6 grams) was introduced into chloroform (300 ml) in a 500 ml flask under stirring and cooling with ice water to obtain a mixture, then an aqueous solution of potassium carbonate (4.5 g) in de-ionized water (40 ml) was added drop by drop into the flask, and it was stirred for one hour. The pH value of the upper aqueous phase was kept over 9. The organic phase was separated and the aqueous phase was extracted with chloroform (150 ml). The organic phases were combined, dried over potassium sulfate and concentrated to the free clopidogrel base.

To the concentrated free base tert-butyl methyl ether (300 ml) was added drop by drop and it was stirred for about one hour until the free base of clopidogrel was completely dissolved.

The solution was cooled to a temperature of −15° C., and then 40% sulfuric acid in tert-butyl methyl ether was added drop by drop at a temperature between −15° C. and −5° C.

After the completion of the drop wise addition the reaction mixture was stirred for another 10 hours at a temperature of −10° C. to 10° C. It was filtered and washed with tert-butyl methyl ether (4×10 ml). It was dried in vacuo between 40° C. and 70° C. and clopidogrel hydrogen sulfate form I (10.7 g) with a specific rotation +52° (c=1, methanol), m.p. 181-186° C., was obtained in a yield of 85%.

It has an X-ray powder diffraction pattern with peaks at 9.2, 10.9, 15.2, 17.9, 18.5, 20.6, 23.0, 23.4 and 25.5±0.2 degree 2 Theta.

It has an infrared spectrum with peaks at 2987, 1753, 1222, 1175 and 841 $cm^{-1}$;

It has a DSC Chromatograph with a melting point of 181-186° C.

Example 5

Under the protection of nitrogen gas, clopidogrel camphor sulfate (5.39 g) was introduced into ethylene dichloride (50 ml) in a 250 ml flask under stirring and cooling with ice water to obtain a mixture. Then a solution of potassium carbonate (1.48 g) in de-ionized water (30 ml) was added drop by drop into the flask and it was stirred for one hour. The pH value of the upper aqueous phase was kept over 9. The organic phase was separated and the aqueous phase was extracted with ethylene dichloride (30 ml). The organic phases were combined, dried over sodium sulfate and concentrated to the free clopidogrel base.

To the concentrated free base, ethyl acetate (150 ml) was added drop by drop and it was stirred for more than one hour until the free base of clopidogrel was completely dissolved.

The solution was cooled to a temperature −5° C., and then 90% sulfuric acid solution (2.2 g) was added drop by drop under controlling the temperature between −20° C. and 5° C. during the drop wise addition.

After the completion of the drop wise addition the reaction mixture was stirred for another 10 hours at a temperature of −20° C. to 20° C. It was filtered and washed with ethyl acetate (4×10 ml). It was dried in vacuo between 50° C. and 55° C. and clopidogrel hydrogen sulfate form I (2.4 g) with a specific rotation +53.7° (c=1, methanol), m.p. 182-183° C., was obtained in a yield of 57%.

Example 6

Under the protection of nitrogen gas, clopidogrel hydrochloride (7.15 g) was introduced into methylene dichloride (100 ml) in a 250 ml flask under stirring and cooling with ice water. Then a solution of potassium carbonate (2.5 g) in de-ionized water (30 ml) was added drop by drop into the flask and it was stirred for one hour. The pH value of the upper aqueous phase was kept over 9. The lower organic phase was separated and the aqueous phase was extracted with methylene dichloride (50 ml). The organic phases were combined and dried over sodium sulfate and then concentrated to obtain a free clopidogrel base.

To the concentrated free base methyl acetate (150 ml) was added drop by drop under stirring for one hour until the free clopidogrel base was completely dissolved.

The complete solution was cooled to a temperature of −10° C., and then concentrated sulfuric acid (2 g) was added drop by drop at a temperature between −5° C. and 5° C.

After the completion of the drop wise addition the reaction mixture was stirred for another 10 hours at a temperature of 0 to 15° C. It was filtered and washed with methyl acetate (4×10 ml). It was dried in vacuo between 50° C. and 55° C. and clopidogrel hydrogen sulfate form I (5.4 g) with a specific rotation +54.1° (c=1, methanol), m.p. 182.3-183.5° C., was obtained in the yield of 64%.

Example 7

Under the protection of nitrogen gas, clopidogrel camphor sulfate (10.78 g) was introduced into isopropyl ether (100 ml) in a 250 ml flask under stirring and cooling with ice water. Then a solution of potassium carbonate (2.2 g) in de-ionized water (50 ml) was added drop by drop into the reactor and it was stirred for one hour. The pH value of the upper aqueous phase was kept over 9. The lower organic phase was separated and the aqueous phase was extracted with isopropyl ether (50 ml). The organic phases were combined and dried over potassium sulfate, then concentrated.

To the concentrated free base, isopropyl ether (150 ml) was added and it was stirred for about one hour until the free clopidogrel base was completely dissolved.

The complete solution was cooled to a temperature of −10° C., and then the relatively concentrated sulfuric acid was added drop by drop at a temperature between −5° C. and 5° C. After the completion of the drop wise addition, the reaction mixture was stirred for another 10 hours at a temperature between −5° C. and 15° C. It was filtered and washed with isopropyl ether (4×10 ml). It was dried in vacuo between 50° C. and 55° C. and clopidogrel hydrogen sulfate form I (4.2 g) with a specific rotation +53.5° (c=1, methanol), m.p. 182-183° C., was obtained in a yield of 50%.

Example 8

Under nitrogen gas, clopidogrel hydrochloride (7.15 g) was introduced into methylene dichloride (100 ml) in a 250 ml reactor under stirring and cooling with ice water to obtain a mixture. Then a solution of potassium carbonate (2.5 g) in de-ionized water (30 ml) was added drop by drop into the reactor and it was stirred for one hour. The pH value of the upper aqueous phase was kept over 9. The organic phase was separated and the aqueous phase was extracted with dichloromethane (2×50 ml). The organic phases were combined, dried over $Na_2SO_4$ and concentrated to a free clopidogrel base.

To the concentrated free base, methyl acetate (150 ml) and methylene dichloride (15 ml) was added and it was stirred for more than one hour until the free base of clopidogrel was completely dissolved.

The solution was cooled to a temperature between −15° C. and −5° C., then 10% sulfuric acid in methylene dichloride (2 g) was added drop by drop under controlling the temperature between −15° C. and −10° C. during the dropwise addition. After the completion of the dropwise addition the reaction mixture was stirred for another 20 hours. It was filtered and washed with methyl acetate (4×10 ml). It was dried in vacuo between 50° C. and 55° C. and clopidogrel hydrogen sulfate form I (4.9 g) with a specific rotation +54.1° (c=1, methanol), m.p. 181.3-182.5° C., was obtained in a yield of 56%.

Example 9

Under nitrogen gas, a crystalline mixture of clopidogrel hydrogen sulfate (8.7 kg) was introduced into dichloromethane (100 L) in a 250 L reactor under stirring and cooling with cool water. Then a solution of potassium carbonate (3.0 kg) in de-ionized water (50 L) was added drop by drop into the reactor and it was stirred for one hour. The pH value of the upper aqueous phase was kept over 8. The lower organic phase was separated and the aqueous phase was extracted with dichloromethane (2×50 L). The organic phases were combined and dried over $Na_2SO_4$, then concentrated. To the concentrated free base ethyl acetate (130 L) and isopropyl ether (20 L) was added and it was stirred for half an hour until the free clopidogrel base was completely dissolved.

The complete solution was cooled to a temperature between −15° C. and −5° C., then concentrated sulfuric acid (1.9 kg) in Ethyl Acetate (30 l) was added drop by drop at a temperature between −10° C. and 0° C. After the completion of the dropwise addition the reaction mixture was stirred for another 5 hours. It was filtered and washed with ethyl acetate (3×2 l). It was dried in vacuo between 50° C. and 55° C. and clopidogrel hydrogen sulfate form I (4.9 kg) with a specific rotation +53.7° (c=1, methanol), m.p, 181.2-182.3° C., was obtained in a yield of 65%.

The invention claimed is:

1. Process for the preparation of crystalline (+)-(S) clopidogrel hydrogen sulfate of polymorphic form I, comprising
   (a) optionally converting a clopidogrel salt into clopidogrel base by addition of a base to a clopidogrel salt,
   (b) dissolving a clopidogrel base in a solvent selected from the group consisting of a mixture of ethyl acetate with methylene chloride or a mixture of ethyl acetate with an ether,
   (c) reacting the solution of clopidogrel base from step (b) with sulfuric acid, and
   (d) recovering clopidogrel hydrogen sulfate of form I.

2. Process for the preparation of crystalline (+)-(S) clopidogrel hydrogen sulfate of polymorphic form I comprising,
   (a) dissolving clopidogrel base in a solvent selected from the group consisting of ethyl ether, ethyl formate, ethyl acetate, methyl acetate, isopropyl ether, methylene chloride and t-butyl methyl ether,
   (b) reacting the solution of clopidogrel base obtained in step (a) with sulfuric acid, and
   (c) recovering clopidogrel hydrogen sulfate of form I.

3. Process according to claim 1, wherein a mixture of ethyl acetate with methylene chloride is used in step (b) which comprises 1 to 5% by weight of methylene chloride.

4. Process according to claim 1, wherein a mixture of ethyl acetate with an ether is used in step (b) which comprises up to 30% by weight of ether.

5. Process according to claim 4, wherein the ether contains up to 10 carbon atoms.

6. Process according to claim 2, wherein the sulfuric acid is used in form of a solution in a solvent.

7. Process according to claim 6, wherein the solvent is ethyl acetate.

8. Process according to claim 2, wherein 0.6-1.1 equivalents of sulfuric acid relative to clopidogrel base are used.

9. Process according to claim 2, wherein the temperature of the mixture obtained during the reaction of step (c) is kept in the range of −20 to 20° C.

10. Process according to claim 1, wherein step (a) is performed by neutralizing a clopidogrel salt with an aqueous inorganic base.

11. Process according to claim 10, including the further step of dissolving the clopidogrel salt in an organic solvent, selected from a group consisting of methylene chloride, chloroform, or an alkyl acetate prior to addition of the base in step (a) of the process.

12. Process according claim 2, wherein the reaction mixture obtained after completion of step (c) is maintained 5-15 hours at a temperature of −10 to 0° C. with stirring.

13. The process according to claim 9, wherein the temperature of the mixture obtained during the reaction of step (c) is kept in the range of −10 to 10° C.

14. Process according to claim 1, wherein the sulfuric acid is used in form of a solution in an organic solvent.

15. Process according to claim 14, wherein the organic solvent is ethyl acetate.

16. Process according to claim 14, wherein the solution of sulfuric acid in an organic solvent is prepared at a temperature of less than 0° C.

17. Process according to claim 14, wherein the solution of sulfuric acid in an organic solvent is prepared at a temperature between −5 to −15° C.

18. Process according to claim 1, wherein up to 0.9 equivalents of sulfuric acid relative to clopidogrel base are used.

19. Process according to claim 1, wherein the temperature of the mixture obtained during the reaction of step (c) is kept in the range of −20 to 5° C.

20. The process according to claim 19, wherein the temperature of the mixture obtained during the reaction of step (c) is kept in the range of −15 to 0° C.

21. Process according to claim 18, wherein the reaction mixture obtained after completion of step (c) is allowed to warm to room temperature with stirring at a heating rate of 0.5 to 6° C. per hour.

22. Process according claim 1, wherein the reaction mixture obtained after completion of step (c) is maintained for at least 1 hour at a temperature of −15 to 0° C. with stirring.

23. Process according claim 1, wherein the reaction mixture obtained after completion of step (c) is maintained 2 to 4 hours at a temperature of −15 to 0° C. with stirring.

* * * * *